United States Patent [19]

Hitzel et al.

[11] 3,998,968
[45] Dec. 21, 1976

[54] BENZENESULFONYL UREAS AND PROCESS FOR THEIR MANUFACTURE

[75] Inventors: Volker Hitzel, Lorsbach, Taunus; Werner Pfaff, Hofheim, Taunus; Rudi Weyer, Kelkheim, Taunus; Helmut Weber, Schneidhain, Taunus, all of Germany

[73] Assignee: Hoechst Aktiengesellschaft, Frankfurt am Main, Germany

[22] Filed: Mar. 19, 1975

[21] Appl. No.: 559,712

[30] Foreign Application Priority Data

Mar. 21, 1974    Germany ........................... 2413514

[52] U.S. Cl. ........................ 424/321; 260/553 D; 260/553 DA; 424/322
[51] Int. Cl.² ................................ C07C 127/00
[58] Field of Search ............... 260/553 DA, 553 D; 424/321, 322

[56] References Cited

UNITED STATES PATENTS

| | | | |
|---|---|---|---|
| 3,013,072 | 12/1961 | McLamore et al. | 260/553 D |
| 3,021,368 | 2/1962 | Blank et al. | 260/553 D |
| 3,426,067 | 2/1969 | Weber et al. | 260/553 DA |
| 3,439,033 | 4/1969 | Haack et al. | 424/321 |
| 3,448,149 | 6/1969 | Aumuller et al. | 260/553 DA |
| 3,454,635 | 8/1969 | Weber et al. | 260/553 DA |
| 3,631,205 | 12/1971 | Frey | 424/322 |
| 3,646,009 | 2/1972 | Winter et al. | 260/553 DA |
| 3,812,185 | 5/1974 | Weber et al. | 260/553 DA |
| 3,825,665 | 7/1974 | Weber et al. | 260/553 D |
| 3,835,188 | 9/1974 | Weyer et al. | 260/553 DA |

FOREIGN PATENTS OR APPLICATIONS

| | | |
|---|---|---|
| 1,558,886 | 1/1969 | France |
| 1,031,088 | 5/1966 | United Kingdom |
| 1,122,820 | 8/1968 | United Kingdom |

OTHER PUBLICATIONS

Momose et al., Chem. Abstracts, 1961, Col. 27177i.
Boggianno et al., J. Pharm. & Pharma. Col. 13, pp. 567-574.

Primary Examiner—Arthur P. Demers
Attorney, Agent, or Firm—Curtis, Morris & Safford

[57] ABSTRACT

N-acylaminoalkyl-benzenesulfonyl-N'-methyl ureas, especially those of the general formula

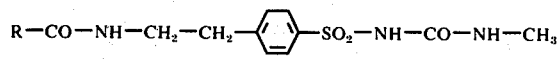

in which R is $C_1$—$C_4$—alkyl or a phenyl radical substituted in 2-position by alkoxy of 1 to 4 carbon atoms, phenoxy or dimethylamino and in 5-position by H, $CH_3$, Cl or Br, their manufacture and their use as oral antidiabetics.

9 Claims, No Drawings

BENZENESULFONYL UREAS AND PROCESS FOR THEIR MANUFACTURE

The present invention relates to benzenesulfonyl ureas and a process for their manufacture.

Sulfonyl ureas are of great importance in the treatment of diabetes millitus. They help diabetics to avoid insulin injection and can be taken in the form of tablets, which is much more comfortable.

The administration of sulfonyl ureas, related compounds and insulin causes hypoglycemia in some cases (cf. H. S. Seltzer, Diabetes 21, 955 (1972), that is to say, the blood sugar level falls below the standardized value. Consequences thereof may be sweating, wolfish hunger, trembling and a narrowed consciousness. Such hypoglycemiae can be caused by various circumstances, for example, irregular ingestion, the outbreak of another disease at the same time, the administration of other medicaments at the same time, overdosage etc.

The present invention is based on the knowledge, that determined sulfonyl ureas, when administered orally, can lower an increased blood sugar level, but do not affect a normal blood sugar level. Benzenesulfonyl ureas having that property are especially those which carry a methyl group at the nitrogen atom of the urea molecule not joined to the sulfonyl group. Especially effective are N-acylaminoalkyl-benzenesulfonyl-N'-methyl ureas in which the acyl group is an organic carboxylic acid radical.

The present invention provides N-acylaminoalkyl-benzenesulfonyl-N'-methyl ureas, especially those of the general formula

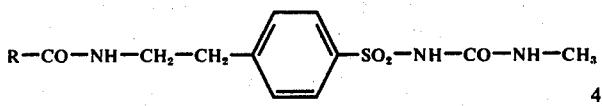

in which R is C$_1$ — C$_4$-alkyl or a phenyl radical substituted in 2-position by alkoxy of 1 to 4 carbon atoms, phenoxy or dimethylamino and in 5-position by H, CH$_3$, Cl or Br.

This invention also provides a process for the manufacture of the sulfonyl ureas as described before, which process comprises a. reacting acylaminoalkylbenzenesulfonyl isocyanates, -carbamic acid esters, -thiolcarbamic acid esters, -ureas, -semicarbazides or -semicabazones with methyl amine or the salts thereof or reacting acylaminoalkyl-benzenesulfonamides or the salts thereof with methyl isocyanate, methylcarbamic acid esters, methyl carbamic acid thiolesters, methylcarbamic acid halides or methyl ureas, b. splitting N-acylaminoalkylbenzenesulfonyl-N'-methyl-isourea-ethers, -isothiourea ethers, -parabanic acids or -haloformic acid amidines or compounds of the general formula

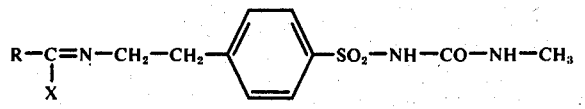

in which R is an organic radical and X is S-low-molecular alkyl, O-low-molecular alkyl or halogen, preferably chlorine;

c. substituting the sulfur atom in N-acylaminoalkyl-benzenesulfonyl-N'-methyl thioureas or N-thioacylaminoalkyl-benzenesulfonyl-N'-methyl ureas by an oxygen atom;

d. adding water to N-acylaminoalkylbenzenesulfonyl-N'-methylcarbodiimides;

e. oxidizing N-acylaminoalkylbenzenesulfonyl or -sulfenyl-N'-methyl ureas;

f. acylating benzenesulfonyl ureas of the formula

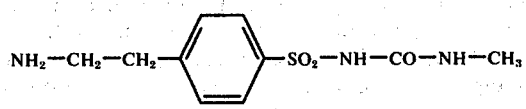

or g. reacting acylaminoalkylbenzenesulfonyl halides with methyl urea or its alkali metal salts or reacting alkylaminoalkyl-benzenesulfinic acid halides or, in the presence of acid condensation agents, correspondingly substituted sulfinic acids or their alkali metal salts with N-methyl-N'-hydroxy urea and optionally treating the reaction products with alkaline agents to cause the formation of salt.

The aforesaid benzenesulfonyl-carbamic acid esters or benzenesulfonylthiocarbamic acid esters may carry in the alcoholic component an alkyl group or an aryl group or even a heterocyclic radical. Since this radical is split off during the reaction, its chemical constitution has no influence on the nature of the final product and may, therefore, be varied within wide limits. The same applies to the methyl carbamic acid esters and the methylthiolcarbamic acid esters.

As carbamic acid halides, the chlorides are preferably used.

The benzenesulfonyl ureas used as starting materials in the process of the present invention may be unsubstituted or substituted once or twice at the nitrogen atom of the urea group not joined to the sulfonyl group. Since these substituents are split off during the reaction with amines their nature may be varied within wide limits. In addition to benzenesulfonyl ureas which carry substituents, there may also be used benzenesulfonyl-carbamoyl imidazoles and similar compounds or bis-(benzenesulfonyl)-ureas which may carry at one of the nitrogen atoms a further substituent, for example a methyl group. For example, such bis-(benzenesulfonyl)-ureas or N-benzenesulfonyl-N'-acyl ureas may be treated with methyl amine and the salts thus obtained may be heated to elevated temperatures, especially to above 100° C.

Furthermore, it is possible to start from methyl ureas which are mono- or, especially, disubstituted at the free nitrogen atom and to react them with acylaminoalkyl-benzenesulfonamides or the salts thereof. As such starting materials, there may be used, for example, N,N'-dimethyl urea and N-methyl-substituted N'-acetyl, N'-nitro, N',N'-diphenyl (in which case the two phenyl radicals may also be substituted or be linked with each other either directly or by means of a bridge member such, for example, as —CH$_2$—, —NH—, —O— or —S— or N', N'-dimethyl ureas and methyl carbamoyl-imidazoles, -pyrazoles or -triazoles.

The benzenesulfonyl parabanic acids, benzenesulfonyl isourea ethers, benzenesulfonyl isothiourea ethers or benzenesulfonyl halo formic acid amidines are advantageously hydrolized by alkaline hydrolysis, isourea ethers can also be split in an acid medium with good success.

The replacement of the sulfur atom in the urea grouping of the correspondingly substituted benzenesulfonyl thioureas by an oxygen atom may be effected in known manner, for example with the aid of an oxide or a salt of a heavy metal or with the use of an oxidizing agent, such, for example, as hydrogen peroxide, sodium peroxide, nitrous acid or permanganates.

The thioureas may also be desulfurized by treating them with phosgen or phosphorous pentachloride. Chloroformic acid amidines or carbodiimides obtained as intermediates may be converted into the benzenesulfonyl ureas by means of adequate measures, for example saponification or addition of water.

Carbodiimides to which water is added according to method (d) may be obtained, for example, from correspondingly substituted thioureas.

As regards the reaction conditions, the manner of carrying out the process of the invention may in general be varied within wide limits, and may be adapted to each individual case. For example, the reactions may be carried out in the presence or absence of a solvent, at room temperature or at an elevated temperature.

Depending on the nature of the starting substances one or the other of the aforesaid methods may, in some cases, provide a desired benzenesulfonyl urea only in a small yield or may be inappropriate for its synthesis. In such comparatively rare cases, the expert will have no difficulty in synthesising the desired product according to one of the other methods of the process described.

The starting materials required for the synthesis of the sulfonyl ureas of the invention are mostly known compounds — especially those used in manufacturing method (a) — or they can be prepared by those skilled in the art without any difficulties according to known methods. The sulfonyl-isourea ethers or isothiourea ethers used in manufacturing method (b) can be obtained by reacting the sulfochlorides with methyliso(-thio)urea ethers, the parabanic acids by reacting the correspondingly substituted benzenesulfonyl chlorides with methylparabanic acid and the halogenated formic acid amidines by treating sulfonylthioureas with phosgen. Compounds of the general formula

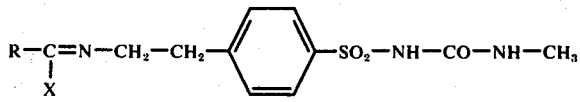

are obtained, for example, by treating a thioamide

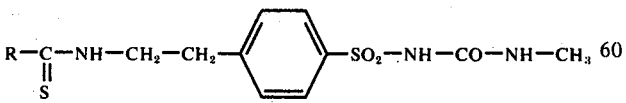

with methyl iodide.

The thioureas mentioned in method (c) are obtained, like the analogous ureas, for example by reacting the acylaminoalkyl sulfonamide with methylisothiocyanate. The thio-acylamido-alkyl-benzenesulfonyl ureas are obtained, for example, by sulfurizing the acylamino-alkyl-benzenesulfonamides with $P_2S_2$ and reacting the reaction products with methylisocyanate.

The carbodiimides can be obtained, for example, by treating the thioureas with mercuric oxide. The benzene-sulfinyl ureas or benzenesulfenyl ureas — which are further worked according to method (e), are obtained, for example, by reacting corresponding sulfinyl halides or sulfenyl halides with methyl urea.

The aminoalkylbenzenesulfonyl ureas of method (f) are obtained in a manner analogous to the corresponding acylated compounds, in which case, in general, the free amino group has to be protected by suitable measures, such as acylation, preferably acetylation, in the synthesis steps required (for example, in the reaction of sulfonamides with methyl carbamic acid esters or with methyl urea). The benzenesulfonyl halides of method (g) are obtained by sulfochlorinating the correspondingly acylated phenylethyl amines. The sulfochlorides obtained can be converted into the corresponding sulfinic acids by treating them with sodium sulfite.

The activity of the sulfonyl ureas described on the increased blood sugar level can be determined as follows:

Firstly, the preparation is examined on sound, normally fed test animals, for which purpose the free compound or the sodium salt is administered, for example, to rabbits via the oral route and the blood sugar level is determined over a prolonged period of time according to the method of Hagedorn-Jensen or by means of an auto-analizer. In this test arrangement, the sulfonylureas described do not lower the blood sugar level. Thereafter, the preparation is administered to rabbits or to other test animals in which experimentally, for example, by administering a glucose dose, an increased blood sugar level is procreated, and the change of the blood sugar level is observed over a prolonged period of time. The two test groups are compared with control animals treated in the same manner, however, without having administered to them any preparation.

The benzenesulfonyl-ureas of the present invention are preferably used for the manufacture of pharmaceutical preparations suitable for oral administration for the lowering of the blood sugar level, and may be used as such or in the form of their physiologically tolerable salts or in the presence of substances which bring about salt formation. For the formation of salts, there may be used, for example, alkaline agents, for example, alkali metal- or alkaline-earth metal-hydroxides and alkali metal or alkaline earth metal-carbonates or bicarbonates.

The pharmaceutical preparations of the invention are preferably formulated as tablets which comprise in addition to the products of the invention the usual, pharmaceutically suitable carriers, for example, talc, starch, lactose, tragacanth or magnesium stearate.

A pharmaceutical preparation, for example, a tablet or a powder, comprising a benzenesulfonyl-urea of the invention or a physiologically tolerable salt thereof as the active substance, with or without one or more of the aforesaid carriers, is advantageously brought into a suitable dosage unit form. The dose chosen should comply with the activity of the benzenesulfonyl-urea and with the desired effect. Advantageously, each dosage unit contains from about 10 to 1000 mg, preferably from 50 to 500 mg, of active substances, but considerably higher or lower dosage units may also be used, which, when required, may be divided or multiplied prior to their administration.

The sulfonyl ureas of the invention can be used for the treatment of *diabetes mellitus*, alone or in combination with other oral antidiabetics. Those antidiabetics are not only sulfonyl ureas having hypoglycemic activity, but also compounds having a different chemical structure, for example, biguanides, especially phenylethyl-biguanide or dimethyl-biguanide. The sulfonyl ureas can also be used in combination with other medicaments, for example, hypolipemic agents.

The following Examples illustrate the invention:

EXAMPLE 1:

N-[4-(β-<5-chloro-2-methoxy-benzamido>-ethyl)-benzene-sulfonyl]-N'-methyl-urea 7.4 g (0.02 mol) of 4-[β-(5-chloro-2-methoxy-benzamido)-ethyl]-benzenesulfonamide were suspended in 150 ml of acetone and cooled to 0°–5° C after the addition of 10 ml of 2 N sodium hydroxide solution. While stirring and further cooling, a solution of 1.3 g of methylisocyanate in 5 ml of acetone was added dropwise. The suspension was heated to room temperature while stirring and stirring was continued at room temperature for 4 hours. Water was added to dilute to three times the volume, undissolved substances were filtered off and the filtrate was acidified with 2 N hydrochloric acid while stirring. The precipitate was suction-filtered, dissolved in 0.2 l of 0.25 N ammonia solution, undissolved substances were filtered off and the product was precipitated with 2 N hydrochloric acid. After suction-filtering and washing with water, the still somewhat moist filter cake was recrystallized from dimethyl formamide.

N-[4-(β-<5-chloro-2-methoxybenzamido>-ethyl)-benzenesulfonyl]-N'-methyl urea was obtained which melted at 206° – 208° C.

In an analogous manner, there were obtained:

N-[4-(β-<2-methoxy-5-methylbenzamido>-ethyl)-benzenesulfonyl]-N'-methyl-urea, of melting point 180° – 182° C (from ethanoldimethylformamide)

N-[4-(β-<2-methoxy-benzamido>-ethyl)-benzenesulfonyl]-N'-methylurea of melting point 188° – 190° C (from aqueous ethanol)

N-[4-(β-5-chloro-2-ethoxybenzamidoethyl)-benzenesulfonyl]-N'-methyl-urea of melting point 213° – 214° C (from methanoldioxane)

N-[4-(β-5-bromo-2-ethoxybenzamidoethyl)-benzenesulfonyl]-N'-methyl-urea, of melting point 208° – 210° C (from methanol-DMF)

N-[4-(β-2-dimethylaminobenzamidoethyl)-benzenesulfonyl]-N'-methyl-urea, of melting point 160° – 162° C (from methanol-water)

N-[4-(β-5-chloro-2-n-propoxybenzamidoethyl)-benzenesulfonyl]-N'-methyl-urea, of melting point 176° – 177° C (from methanol-DMF)

N-[4-(β-5-chloro-2-phenoxybenzamidoethyl)-benzenesulfonyl]-N'-methyl-urea, of melting point 159° – 161° C (from methanol)

N-[4-(β-acetamidoethyl)-benzenesulfonyl]-N'-methyl-urea, of melting point 213° – 215° C (from ethanol-water)

N-[4-(β-propionamidoethyl)-benzenesulfonyl]-N'-methyl-urea, of melting point 182° – 184° C (from ethanol-water)

N-[4-(β-n-butyramidoethyl)-benzenesulfonyl]-N'-methyl-urea, of melting point 189° – 190° C (from methanol)

N-[4-(β-isobutyramidoethyl)-benzenesulfonyl]-N'-methyl-urea, of melting point 205° – 206° C (from methanol-dioxane)

N-[4-(β-trimethylacetamidoethyl)-benzenesulfonyl]-N'-methylurea, of melting point 214° – 215° C (from methanol).

EXAMPLE 2:

N-[4-(β-<2-methoxy-5-chlorobenzamido>-ethyl)-benzenesulfonyl]-N'-methyl-urea 17 g of N-[4-(β-<2-methoxy-5-chloro-benzamido>-ethyl)-benzenesulfonyl]-carbamic acid methyl ester were suspended in 300 ml of dioxane. After adding 2.8 g of methylamine-hydrochloride and 4 g of triethyl amine the suspension was heated on a descending cooler for 2 hours while stirring and distilling 50 ml of dioxane. After cooling, water was added to dilute to the double volume. The N-[4-(β-<2-methoxy-5-chlorobenzamido>-ethyl)-benzenesulfonyl]-N'-methyl-urea obtained in the form of crystals was recrystallized from methanol/DMF and melted at 207° – 208° C.

We claim:

1. A benzenesulfonyl urea of the formula

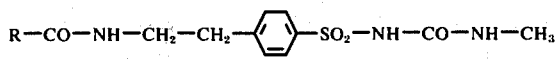

in which R stands for alkyl of 1 to 4 carbon atoms or phenyl which is substituted in 2-position by alkoxy of 1 to 4 carbon atoms, phenoxy or dimethylamino and in 5-position by hydrogen, methyl, chlorine or bromine or the pharmaceutically acceptable salts thereof.

2. A compound as defined in claim 1 in which R is alkyl of 1 to 4 carbon atoms.

3. A compound as defined in claim 1 in which R is phenyl substituted in the 2-position by alkoxy of 1 to 4 carbon atoms, phenoxy or dimethylamino and in the 5-position by hydrogen, methyl, chlorine or bromine.

4. The compound of claim 3 which is N-[4-(β-<5-chloro-2-methoxy-benzamido>-ethyl)-benzenesulfonyl]-N'-methyl-urea.

5. The compound of claim 3 which is N-[4-(β-<2-methoxy-5-methyl-benzamido>-ethyl)-benzenesulfonyl]-N'-methyl-urea.

6. N-[4-(β-acetamidoethyl)-benzenesulfonyl]-N'-methyl-urea.

7. A pharmaceutical composition containing from about 10 to 1,000 mg per dosage unit of a compound as defined in claim 1 and a pharmaceutically suitable carrier therefor.

8. A method of treatment which comprises administering to a diabetic patient a compound as defined in claim 1.

9. The method as defined in claim 3, wherein the compound is administered in a dosage unit of 10 to 1000 mg.

* * * * *